United States Patent
Locker

(10) Patent No.: US 9,017,422 B2
(45) Date of Patent: Apr. 28, 2015

(54) PROSTHETIC WEIGHT-LIFTING TOOL FOR AMPUTEES

(71) Applicant: Sean C. Locker, Littlestown, PA (US)

(72) Inventor: Sean C. Locker, Littlestown, PA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 14/179,294

(22) Filed: Feb. 12, 2014

(65) Prior Publication Data

US 2014/0228975 A1  Aug. 14, 2014

Related U.S. Application Data

(60) Provisional application No. 61/764,663, filed on Feb. 14, 2013.

(51) Int. Cl.
*A61F 2/54* (2006.01)
*A61F 2/58* (2006.01)
*A61F 4/00* (2006.01)
*A61F 2/50* (2006.01)

(52) U.S. Cl.
CPC . *A61F 2/54* (2013.01); *A61F 2/582* (2013.01); *A61F 2/58* (2013.01); *A61F 2002/502* (2013.01); *A61F 2/588* (2013.01); *A61F 4/00* (2013.01)

(58) Field of Classification Search
CPC ............ A61F 2/54; A61F 2/58; A61F 2/582; A61F 2/583; A61F 2/585; A61F 2/586; A61F 2/588; A61F 2/581
USPC ................ 623/57–62, 65, 66.1; 269/181–182
See application file for complete search history.

(56) References Cited

U.S. PATENT DOCUMENTS

| | | | | |
|---|---|---|---|---|
| 3,599,960 A | * | 8/1971 | Phillips | 269/182 |
| 3,833,942 A | * | 9/1974 | Collins | 623/60 |
| 4,038,706 A | | 8/1977 | Ober et al. | 3/12.3 |
| 4,232,405 A | | 11/1980 | Janovsky | 3/12.3 |
| 5,139,526 A | | 8/1992 | Skardoutos et al. | 623/59 |
| 5,163,966 A | | 11/1992 | Norton et al. | 623/65 |
| 5,252,102 A | * | 10/1993 | Singer et al. | 623/24 |
| 5,314,500 A | | 5/1994 | Weddendorf | 623/57 |
| 5,888,235 A | * | 3/1999 | Jacobsen et al. | 623/58 |
| 6,250,621 B1 | * | 6/2001 | Ping | 269/181 |
| 6,416,555 B1 | * | 7/2002 | Dillenburg et al. | 623/65 |
| 6,582,473 B2 | | 6/2003 | Pierce et al. | 623/65 |
| 2007/0010772 A1 | * | 1/2007 | Ryan | 602/26 |

OTHER PUBLICATIONS

TRS Weight Lifting Devices. http://www.trsprosthetics.com Verified by the wayback machine 2010.*
Max Grip Barbell Attachment. Youtube. Nov. 11, 2009.*
Texas Assistive Devices Passive Hook. Verified by the wayback machine 2007.*
Texas Assistive Devices Weight Lifting Device. Verified by the wayback machine 2007.*
TRS Adult Grip Prehensors. Verified by the wayback machine 2009.*

* cited by examiner

*Primary Examiner* — Thomas J Sweet
*Assistant Examiner* — Christie Bahena
(74) *Attorney, Agent, or Firm* — Gerhard W. Thielman, Esq.

(57) ABSTRACT

A prosthetic instrument is provided for attaching to a forearm shaft of an upper limb amputee to enable receipt of a handle, such as a weight-lifting barbell. The instrument includes a rod having a proximal end for receiving the forearm shaft and a distal end; and a yoke having a pair of prongs that extend from a bridge that connects to the distal end, wherein said pair of prongs provide a gap into which to insert the handle. Each prong includes a through-hole along a common axis to accommodate a clamp pin to secure the handle.

4 Claims, 2 Drawing Sheets

PROSTHETIC WEIGHT-LIFTING TOOL FOR AMPUTEES

CROSS REFERENCE TO RELATED APPLICATION

Pursuant to 35 U.S.C. §119, the benefit of priority from provisional application 61/764,663, with a filing date of Feb. 14, 2013, is claimed for this non-provisional application.

STATEMENT OF GOVERNMENT INTEREST

The invention described was made in the performance of official duties by one or more employees of the Department of the Navy, and thus, the invention herein may be manufactured, used or licensed by or for the Government of the United States of America for governmental purposes without the payment of any royalties thereon or therefor.

BACKGROUND

The invention relates generally to prosthetics. In particular, the invention relates to a weight-lifting tool to aid an upper limb amputee, i.e., a person who has lost an arm.

Military service personnel operating in combat zones and other persons involved in hazardous occupations risk being subject to tissue damage to extremities, such as arms and legs, to a degree as to require surgical amputation. The unfortunate experience can produce consequences of physical pain, disfigurement and inconvenience regarding activities pursued prior to severe injury.

An example of such inconvenience involves weight-lifting, such as with a bench-press. Human hands can provide subtle and effective grip of properly shaped tools, such as rod handles. Arms and shoulders employ muscles and joints that enable exercise, such as lifting balanced objects of appreciable mass. Such operations are severely compromised by loss of a hand and/or an elbow, reducing rotational flexibility as well as handling capacity.

SUMMARY

Conventional prosthetics yield disadvantages addressed by various exemplary embodiments of the present invention. In particular, various exemplary embodiments provide a prosthetic instrument for attaching to a forearm shaft of an upper limb amputee to enable receipt of a handle, such as a weight-lifting barbell. The instrument includes a rod having a proximal end for receiving the forearm shaft and a distal end; and a yoke having a pair of prongs that extend from a bridge that connects to the distal end, wherein said pair of prongs provide a gap into which to insert the handle. Each prong includes a through-hole along a common axis to accommodate a clamp pin to secure the handle.

BRIEF DESCRIPTION OF THE DRAWINGS

These and various other features and aspects of various exemplary embodiments will be readily understood with reference to the following detailed description taken in conjunction with the accompanying drawings, in which like or similar numbers are used throughout, and in which.

DETAILED DESCRIPTION

In the following detailed description of exemplary embodiments of the invention, reference is made to the accompanying drawings that form a part hereof, and in which is shown by way of illustration specific exemplary embodiments in which the invention may be practiced. These embodiments are described in sufficient detail to enable those skilled in the art to practice the invention. Other embodiments may be utilized, and logical, mechanical, and other changes may be made without departing from the spirit or scope of the present invention. The following detailed description is, therefore, not to be taken in a limiting sense, and the scope of the present invention is defined only by the appended claims.

Figure 1:
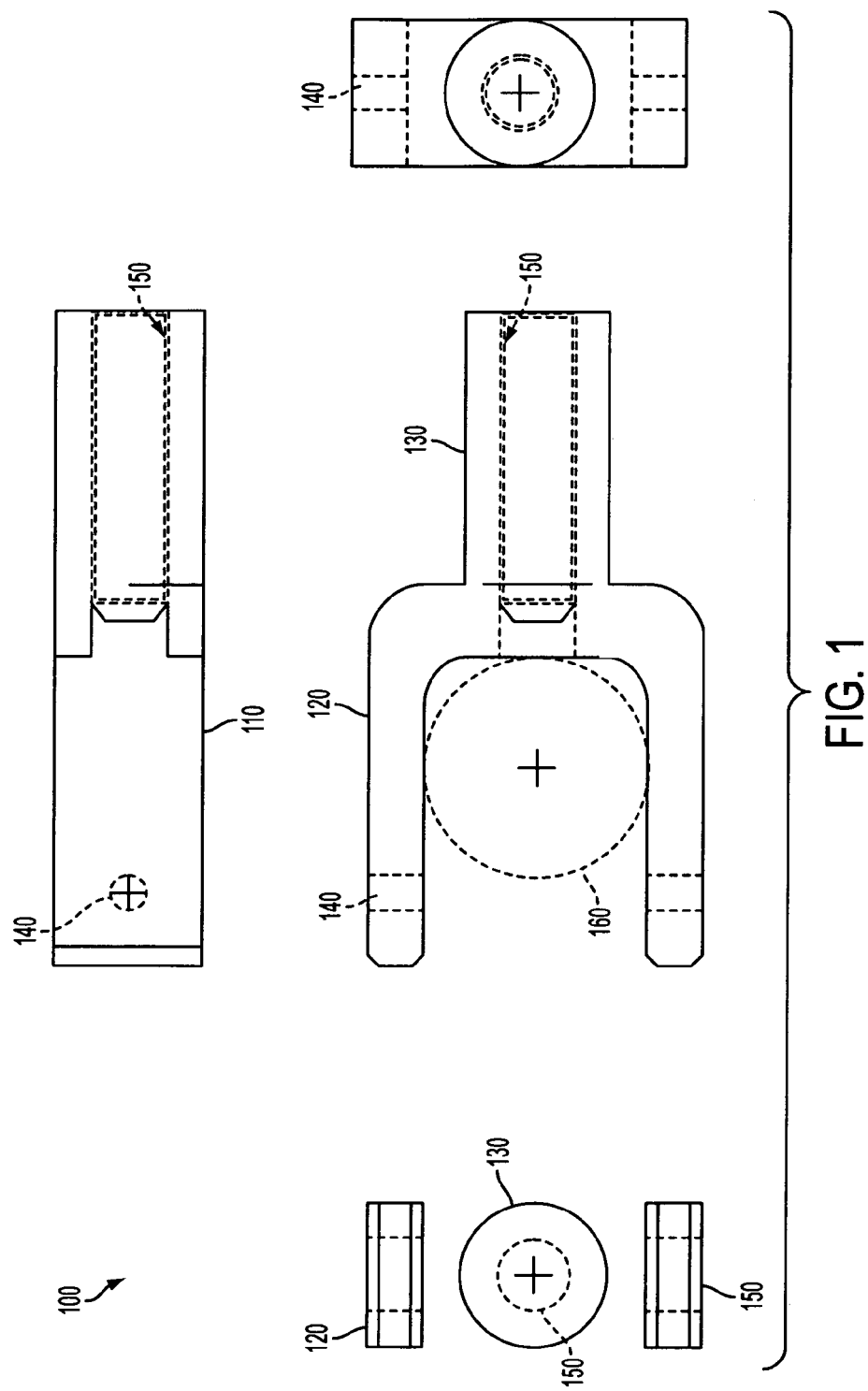
FIG. 1 is a set of views of a yoke adaptor.

The inventor is a left-above-the-elbow (trans-humeral) amputee who was active in weightlifting prior to losing his left arm. After realizing a lack of any suitable prosthetics available to above-the-elbow amputees for weight-lifting, the inventor decided to fabricate his own. FIG. 1 shows a multiple views 100 of a prosthetic yoke adaptor 110. An elevation view of the yoke adaptor 110 is shown at upper center. A plan view is shown at lower center. Fore and aft views are respectively shown to the left and right of the elevation view.

The yoke adaptor 110 includes a fork 120 and a central threaded rod 130. The U-shaped fork 120 includes a through-hole 140 having a centerline that extends across both prongs that extend from a bridge that connects to the rod 130 at its distal end. The rod 130 includes a center threaded countersunk hole 150 at its proximal end. A circular outline 160 illustrates a location between the prongs of the fork 120 and the rod 130 in which a weight-lifting bar can be inserted for bench-pressing or other exercises.

The views 100 denote exemplary dimensions for the adaptor 110. The distance between facing surfaces of the fork 120 is 1.50 inches to accommodate cylindrical device, such as a barbell handle. The through-hole 140 has a diameter of 0.25 inch to accommodate a restraining pin.

Figure 2:
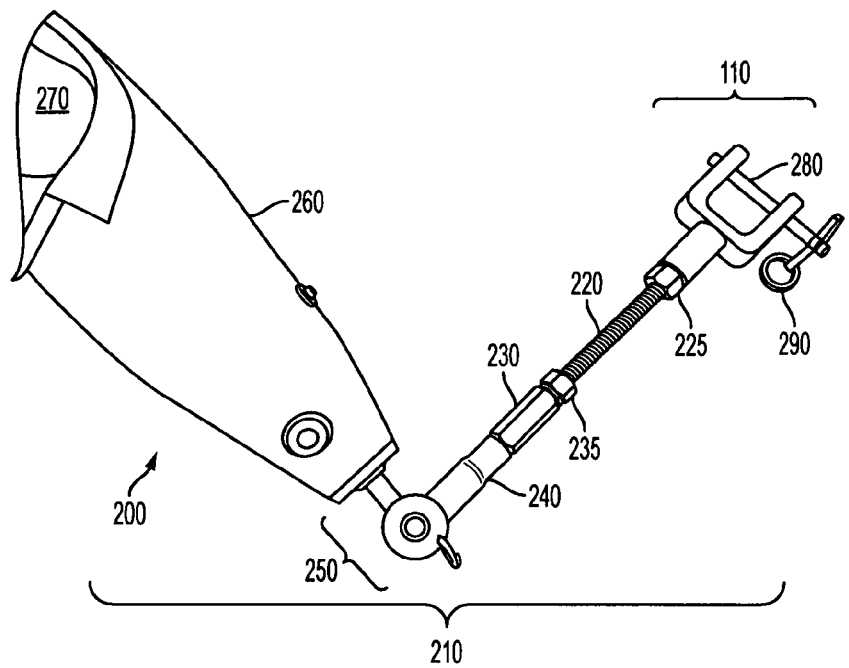
FIG. 2 is a perspective photographic view of a prosthetic assembly equipped with the exemplary adaptor.

FIG. 2 shows a perspective view 200 of a prosthetic assembly 210 with the adaptor 110. At its distal end, a shaft 220 screws into to the rod 130 and is secured by a first jam nut 225 (e.g., a nylon insert supplemented with a threaded lock nut). At its proximal end, the shaft 220 screws into a sleeve 230 and secured by a second jam nut 235. The sleeve 230 attaches longitudinally onto a clevis 240 that pivotably connects to a heim joint 250 into its attachment opening. An arm socket 260 includes at its proximal end an insertion opening 270 for receiving the amputee's humerus residual. The arm socket 260 attaches to the heim joint 250 by its joint shaft.

Figure 3:
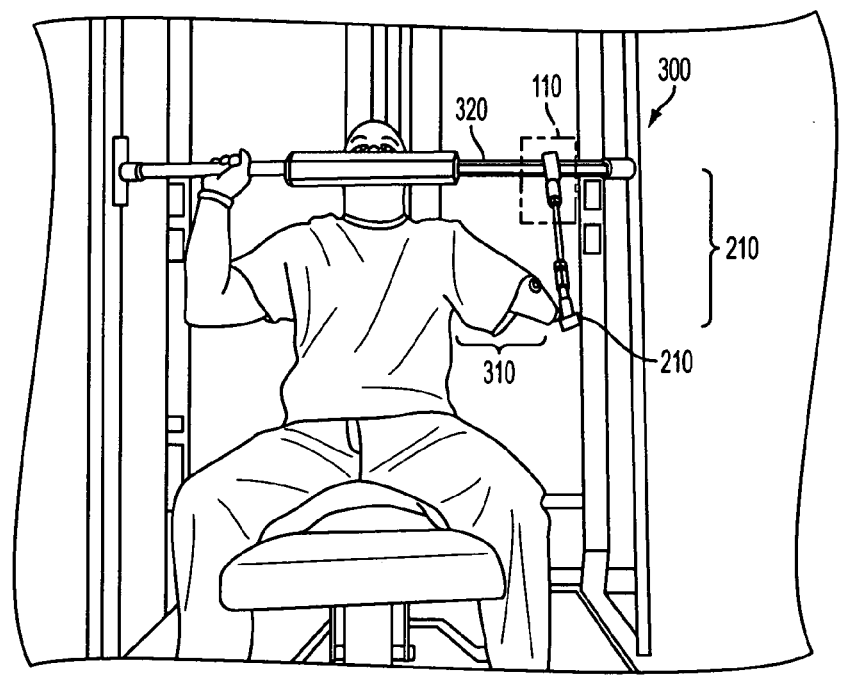
FIG. 3 is a perspective photographic view of an operator using the exemplary prosthetic assembly.

After attaching the prosthetic 210, an amputee operator can insert an exercise tool, e.g., a barbell handle into the yoke 120. A clamp pin 280 secures the handle to the yoke 120 until removal of the lock release pin 290. FIG. 3 shows a perspective view 300 of an operator engaged in bench-pressing weights using the adaptor 110. The operator wears the prosthetic assembly 210 attached to the left humerus 310 below the shoulder. The heim joint 250 angles to position the forearm upright and enable the yoke 120 on the adaptor 110 to receive a barbell handle 320. Thus, the operator can lift the barbell handle 320 using both arms for purposes of weight-training.

The heim joint 250 is also known as a rod end bearing and can be used for precision articulation. The heim joint 250 includes a casing, a spherical swivel within the casing, an opening for hardware attachment, and a joint shaft extending from the casing. The joint shaft can be threaded or solid, depending on application. The amputee's elbow includes the heim joint 250, with its ½"×20 extension shaft, and the ½"×13 clevis 240, with a quick release pin that secures them together.

The ½"-13 fully threaded rod 130 acts as a wrist connected to the shaft 220 that acts as a forearm. The custom machined fork 120, or yoke end, equipped with the quick-release pin 280 acts as the hand. The pin 280 inserts into the through-holes 140 of the yoke 120. The threaded rod 130 attaches to the base of the fork via female ½"×13 threads. This method of attachment enables the length of the arm assembly to be quickly adjusted for length in the event of misalignment with barbells or exercise machines. This prosthetic 110 is inexpensive and easy to produce but still enables amputees to weight-lift again and enhance their physical fitness. In addition, the prosthetic 110 can be used by a below-the-elbow amputee as a forearm attachment for similar purposes.

While certain features of the embodiments of the invention have been illustrated as described herein, many modifications, substitutions, changes and equivalents will now occur to those skilled in the art. It is, therefore, to be understood that the appended claims are intended to cover all such modifications and changes as fall within the true spirit of the embodiments.

What is claimed is:

1. A prosthetic component for attaching to a transhumeral socket of an upper limb amputee to enable receipt of a handle, said component comprising: a heim joint that attaches to the transhumeral socket and is configured to act as an elbow joint, a forearm shaft that attaches to said heim joint; a rod having a proximal end for receiving said forearm shaft and a distal end; and a yoke having a pair of prongs that extend from a bridge that integrates with said distal end, wherein said pair of prongs provide a gap into which to insert the handle.

2. The component according to claim 1, wherein each prong of said pair of prongs includes a through-hole along a common axis to accommodate a clamp pin.

3. The component according to claim 1, wherein the handle is a barbell handle.

4. The component according to claim 1, wherein a longitudinal bore extends from said proximal end through said bridge, said bore being threaded for receiving said forearm shaft.

* * * * *